US012521148B2

(12) United States Patent
Machamer

(10) Patent No.: US 12,521,148 B2
(45) **Date of Patent: *Jan. 13, 2026**

(54) FIXATORS FOR BONE STABILIZATION AND ASSOCIATED SYSTEMS AND METHODS

(71) Applicant: GLOBUS MEDICAL, INC., Audubon, PA (US)

(72) Inventor: David Machamer, Glen Mills, PA (US)

(73) Assignee: Globus Medical Inc., Audubon, PA (US)

( * ) Notice: Subject to any disclaimer, the term of this patent is extended or adjusted under 35 U.S.C. 154(b) by 17 days.

This patent is subject to a terminal disclaimer.

(21) Appl. No.: 18/760,484

(22) Filed: Jul. 1, 2024

(65) Prior Publication Data

US 2024/0350171 A1 Oct. 24, 2024

Related U.S. Application Data

(63) Continuation of application No. 17/676,304, filed on Feb. 21, 2022, now Pat. No. 12,042,180, which is a continuation of application No. 16/411,388, filed on May 14, 2019, now Pat. No. 11,284,920, which is a continuation of application No. 15/708,193, filed on Sep. 19, 2017, now Pat. No. 10,327,815, which is a continuation of application No. 15/058,372, filed on Mar. 2, 2016, now Pat. No. 9,795,411.

(51) Int. Cl.
*A61B 17/62* (2006.01)

(52) U.S. Cl.
CPC .................................... *A61B 17/62* (2013.01)

(58) Field of Classification Search
CPC ...................................................... A61B 17/62
See application file for complete search history.

(56) References Cited

U.S. PATENT DOCUMENTS

| | | | |
|---|---|---|---|
| 1,105,105 | A | 7/1914 | Sherman |
| 2,486,303 | A | 10/1949 | Longfellow |
| 3,463,148 | A | 8/1969 | Treace |
| 3,695,259 | A | 10/1972 | Yost |
| 3,716,050 | A | 2/1973 | Johnston |
| 3,976,061 | A | 8/1976 | Volkov et al. |
| 4,219,015 | A | 8/1980 | Steinemann |
| 4,493,317 | A | 1/1985 | Klaue |
| 4,524,765 | A | 6/1985 | de Zbikowski |
| 4,651,724 | A | 3/1987 | Berentey et al. |

(Continued)

FOREIGN PATENT DOCUMENTS

| | | | |
|---|---|---|---|
| CN | 201987653 | U | 9/2011 |
| CN | 202313691 | U | 7/2012 |

(Continued)

*Primary Examiner* — Nicholas J Plionis

(57) ABSTRACT

The present technology relates generally to ring fixators and associated systems and methods. In some embodiments, for example, a ring fixator assembly comprises a ring configured to surround a fractured bone, a retention device disposed at a first position on the ring, and a tensioner clamp disposed at a second position on the ring. A wire extends between the retention device and the tensioner clamp. The tensioner clamp includes a first screw configured to secure the wire in position with respect to the tensioner clamp and a second screw configured to apply additional tension to the wire.

15 Claims, 7 Drawing Sheets

(56) References Cited

U.S. PATENT DOCUMENTS 4,683,878 A 8/1987 Carter
4,768,524 A 9/1988 Hardy
4,781,183 A 11/1988 Casey et al.
4,867,144 A 9/1989 Karas et al.
4,923,471 A 5/1990 Morgan
4,936,843 A * 6/1990 Sohngen ............ A61B 17/6441 606/56
4,966,599 A 10/1990 Pollock
5,002,544 A 3/1991 Klaue et al.
5,041,114 A 8/1991 Chapman et al.
5,151,103 A 9/1992 Tepic et al.
5,259,398 A 11/1993 Vrespa
5,364,399 A 11/1994 Lowery et al.
5,372,598 A 12/1994 Luhr et al.
5,423,826 A 6/1995 Coates et al.
5,468,242 A 11/1995 Reisberg
D365,634 S 12/1995 Morgan
5,489,305 A 2/1996 Morgan
5,527,311 A 6/1996 Procter et al.
5,578,036 A 11/1996 Stone et al.
5,601,553 A 2/1997 Trebing et al.
5,676,667 A 10/1997 Hausman
5,690,631 A 11/1997 Duncan et al.
5,709,686 A 1/1998 Talos et al.
5,709,687 A 1/1998 Pennig
5,718,704 A 2/1998 Medoff
5,718,705 A 2/1998 Sammarco
5,728,095 A 3/1998 Taylor et al.
5,746,741 A 5/1998 Kraus et al.
5,746,742 A 5/1998 Runciman et al.
5,766,175 A 6/1998 Martinotti
5,766,176 A 6/1998 Duncan
5,779,706 A 7/1998 Tschakaloff
5,785,712 A 7/1998 Runciman et al.
5,797,914 A 8/1998 Leibinger
5,814,048 A 9/1998 Morgan
5,925,048 A 7/1999 Ahmad et al.
5,928,230 A 7/1999 Tosic
5,938,664 A 8/1999 Winquist et al.
5,961,519 A 10/1999 Bruce et al.
5,980,540 A 11/1999 Bruce
6,001,099 A 12/1999 Huebner
6,071,291 A 6/2000 Forst et al.
6,093,201 A 7/2000 Cooper et al.
6,096,040 A 8/2000 Esser
6,107,718 A 8/2000 Schustek et al.
6,152,927 A 11/2000 Farris et al.
6,206,881 B1 3/2001 Frigg et al.
6,283,969 B1 9/2001 Grusin et al.
6,309,393 B1 10/2001 Tepic et al.
6,322,562 B1 11/2001 Wolter
6,364,882 B1 4/2002 Orbay
D458,683 S 6/2002 Bryant et al.
D458,684 S 6/2002 Bryant et al.
6,533,786 B1 3/2003 Needham et al.
D479,331 S 9/2003 Pike et al.
6,623,486 B1 9/2003 Weaver et al.
6,669,700 B1 12/2003 Farris et al.
6,669,701 B2 12/2003 Steiner et al.
6,712,820 B2 3/2004 Orbay
6,719,759 B2 4/2004 Wagner et al.
6,730,091 B1 5/2004 Pfefferle et al.
6,866,665 B2 3/2005 Orbay
6,955,677 B2 10/2005 Dahners
6,974,461 B1 12/2005 Wolter
7,001,387 B2 2/2006 Farris et al.
7,063,701 B2 6/2006 Michelson
7,090,676 B2 8/2006 Huebner et al.
7,128,744 B2 10/2006 Weaver et al.
7,137,987 B2 11/2006 Patterson et al.
7,153,309 B2 12/2006 Huebner et al.
7,179,260 B2 2/2007 Gerlach et al.
7,250,053 B2 7/2007 Orbay
7,294,130 B2 11/2007 Orbay
7,322,983 B2 1/2008 Harris
7,341,589 B2 3/2008 Weaver et al.
7,344,538 B2 3/2008 Myerson et al.
7,354,441 B2 4/2008 Frigg
7,604,657 B2 10/2009 Orbay et al.
7,632,277 B2 12/2009 Woll et al.
7,635,381 B2 12/2009 Orbay
7,637,928 B2 12/2009 Fernandez
7,655,029 B2 2/2010 Niedernberger et al.
7,655,047 B2 2/2010 Swords
7,695,472 B2 4/2010 Young
7,717,946 B2 5/2010 Oepen et al.
7,722,653 B2 5/2010 Young et al.
7,740,648 B2 6/2010 Young et al.
D622,853 S 8/2010 Raven, III
7,771,457 B2 8/2010 Kay et al.
7,776,076 B2 8/2010 Grady, Jr. et al.
7,857,838 B2 12/2010 Orbay
7,867,260 B2 1/2011 Meyer et al.
7,867,261 B2 1/2011 Sixto, Jr. et al.
7,875,062 B2 1/2011 Lindemann et al.
7,905,910 B2 3/2011 Gerlach et al.
7,909,858 B2 3/2011 Gerlach et al.
7,951,178 B2 5/2011 Jensen
7,951,179 B2 5/2011 Matityahu
7,976,570 B2 7/2011 Wagner et al.
D643,121 S 8/2011 Millford et al.
D646,785 S 10/2011 Milford
8,043,297 B2 10/2011 Grady, Jr. et al.
8,057,520 B2 11/2011 Ducharme et al.
8,062,296 B2 11/2011 Orbay et al.
8,100,953 B2 1/2012 White et al.
8,105,367 B2 1/2012 Austin et al.
8,114,081 B2 2/2012 Kohut et al.
8,118,846 B2 2/2012 Leither et al.
8,118,848 B2 2/2012 Ducharme et al.
8,162,950 B2 4/2012 Digeser et al.
8,167,918 B2 5/2012 Strnad et al.
8,177,820 B2 5/2012 Anapliotis et al.
8,246,661 B2 8/2012 Beutter et al.
8,252,032 B2 8/2012 White et al.
8,257,403 B2 9/2012 Den Hartog et al.
8,257,405 B2 9/2012 Haidukewych et al.
8,257,406 B2 9/2012 Kay et al.
8,262,707 B2 9/2012 Huebner et al.
8,267,972 B1 9/2012 Gehlert
8,317,842 B2 11/2012 Graham et al.
8,323,321 B2 12/2012 Gradl
8,337,535 B2 12/2012 White et al.
8,343,155 B2 1/2013 Fisher et al.
8,382,807 B2 2/2013 Austin et al.
8,394,098 B2 3/2013 Orbay et al.
8,394,130 B2 3/2013 Orbay et al.
8,398,685 B2 3/2013 McGarity et al.
8,403,966 B2 3/2013 Ralph et al.
8,419,775 B2 4/2013 Orbay et al.
8,435,272 B2 5/2013 Dougherty et al.
8,439,918 B2 5/2013 Gelfand
8,444,679 B2 5/2013 Ralph et al.
8,491,593 B2 7/2013 Prien et al.
8,506,608 B2 8/2013 Cerynik et al.
8,512,384 B2 8/2013 Beutter et al.
8,512,385 B2 8/2013 White et al.
8,518,090 B2 8/2013 Huebner et al.
8,523,862 B2 9/2013 Murashko, Jr.
8,523,919 B2 9/2013 Huebner et al.
8,523,921 B2 9/2013 Horan et al.
8,540,755 B2 9/2013 Whitmore
8,551,095 B2 10/2013 Fritzinger et al.
8,551,143 B2 10/2013 Norris et al.
8,568,462 B2 10/2013 Sixto, Jr. et al.
8,574,268 B2 11/2013 Chan et al.
8,597,334 B2 12/2013 Mocanu
8,603,147 B2 12/2013 Sixto, Jr. et al.
8,617,224 B2 12/2013 Kozak et al.
8,632,574 B2 1/2014 Kortenbach et al.
8,641,741 B2 2/2014 Murashko, Jr.
8,641,744 B2 2/2014 Weaver et al.
8,663,224 B2 3/2014 Overes et al.
8,728,082 B2 5/2014 Fritzinger et al.

(56) References Cited

U.S. PATENT DOCUMENTS 8,728,126 B2 5/2014 Steffen
8,740,905 B2 6/2014 Price et al.
8,747,442 B2 6/2014 Orbay et al.
8,764,751 B2 7/2014 Orbay et al.
8,764,808 B2 7/2014 Gonzalez-Hernandez
8,777,998 B2 7/2014 Daniels et al.
8,790,376 B2 7/2014 Fritzinger et al.
8,790,377 B2 7/2014 Ralph et al.
8,808,333 B2 8/2014 Kuster et al.
8,808,334 B2 8/2014 Strnad et al.
8,834,532 B2 9/2014 Velikov et al.
8,834,537 B2 9/2014 Castanada et al.
8,852,246 B2 10/2014 Hansson
8,852,249 B2 10/2014 Ahrens et al.
8,858,555 B2 10/2014 Crozet et al.
8,864,802 B2 10/2014 Schwager et al.
8,870,931 B2 10/2014 Dahners et al.
8,888,825 B2 11/2014 Batsch et al.
8,906,076 B2 12/2014 Mocanu et al.
8,911,482 B2 12/2014 Lee et al.
8,926,675 B2 1/2015 Leung et al.
8,940,026 B2 1/2015 Hilse et al.
8,940,028 B2 1/2015 Austin et al.
8,940,029 B2 1/2015 Leung et al.
8,945,128 B2 2/2015 Singh et al.
8,951,252 B2 2/2015 Steiner et al.
8,951,291 B2 2/2015 Impellizzeri
8,968,368 B2 3/2015 Tepic
9,011,457 B2 4/2015 Grady, Jr. et al.
9,023,052 B2 5/2015 Lietz et al.
9,050,151 B2 6/2015 Schilter
9,072,555 B2 7/2015 Michel
9,072,557 B2 7/2015 Fierlbeck et al.
9,107,678 B2 8/2015 Murner et al.
9,107,711 B2 8/2015 Hainard
9,107,713 B2 8/2015 Horan et al.
9,107,718 B2 8/2015 Isch
9,113,970 B2 8/2015 Lewis et al.
9,149,310 B2 10/2015 Fritzinger et al.
9,161,791 B2 10/2015 Frigg
9,161,795 B2 10/2015 Chasbrummel et al.
9,168,075 B2 10/2015 Dell'Oca
9,179,950 B2 11/2015 Zajac et al.
9,179,956 B2 11/2015 Cerynik et al.
9,180,020 B2 11/2015 Gause et al.
9,211,151 B2 12/2015 Weaver et al.
9,259,217 B2 2/2016 Fritzinger et al.
9,259,255 B2 2/2016 Lewis et al.
9,271,769 B2 3/2016 Batsch et al.
9,283,010 B2 3/2016 Medoff et al.
9,295,506 B2 3/2016 Raven, III et al.
9,314,284 B2 4/2016 Chan et al.
9,320,554 B2 4/2016 Greenberg et al.
9,322,562 B2 4/2016 Takayama et al.
9,370,388 B2 6/2016 Globerman et al.
D765,851 S 9/2016 Early et al.
9,433,407 B2 9/2016 Fritzinger et al.
9,433,452 B2 9/2016 Weiner et al.
9,468,479 B2 10/2016 Marotta et al.
9,480,512 B2 11/2016 Orbay
9,486,262 B2 11/2016 Andermahr et al.
9,492,213 B2 11/2016 Orbay
9,510,878 B2 12/2016 Nanavati et al.
9,510,880 B2 12/2016 Terrill et al.
9,526,543 B2 12/2016 Castaneda et al.
9,545,277 B2 1/2017 Wolf et al.
9,549,819 B1 1/2017 Bravo et al.
9,566,097 B2 2/2017 Fierlbeck et al.
9,579,133 B2 2/2017 Guthlein
9,622,799 B2 4/2017 Orbay et al.
9,636,157 B2 5/2017 Medoff
9,649,141 B2 5/2017 Raven, III et al.
9,668,794 B2 6/2017 Kuster et al.
9,801,670 B2 10/2017 Hashmi et al.
9,814,504 B2 11/2017 Ducharme et al.
2002/0045901 A1 4/2002 Wagner et al.
2004/0097937 A1 5/2004 Pike et al.
2005/0107796 A1 5/2005 Gerlach et al.
2005/0131413 A1 6/2005 O'Driscoll et al.
2005/0187551 A1 8/2005 Orbay et al.
2006/0149265 A1 7/2006 James et al.
2006/0241607 A1 10/2006 Myerson et al.
2006/0276786 A1 12/2006 Brinker
2007/0173840 A1 7/2007 Huebner
2007/0270849 A1 11/2007 Orbay et al.
2007/0288022 A1 12/2007 Lutz
2008/0021477 A1 1/2008 Strnad et al.
2008/0234749 A1 9/2008 Forstein
2008/0275510 A1 11/2008 Schonhardt et al.
2009/0024172 A1 1/2009 Pizzicara
2009/0024173 A1 1/2009 Reis, Jr.
2009/0118773 A1 5/2009 James et al.
2009/0198285 A1 8/2009 Raven, III
2009/0228010 A1 9/2009 Gonzalez-Hernandez et al.
2009/0228047 A1 9/2009 Derouet et al.
2009/0248084 A1 10/2009 Hintermann
2009/0281543 A1 11/2009 Orbay et al.
2009/0299369 A1 12/2009 Orbay et al.
2009/0312760 A1 12/2009 Forstein et al.
2010/0057086 A1 3/2010 Price et al.
2010/0114097 A1 5/2010 Siravo et al.
2010/0121326 A1 5/2010 Woll et al.
2010/0274247 A1 10/2010 Grady, Jr. et al.
2011/0106086 A1 5/2011 Laird
2011/0218580 A1 9/2011 Schwager et al.
2012/0010667 A1 1/2012 Eglseder
2012/0059424 A1 3/2012 Epperly et al.
2012/0203227 A1 8/2012 Martin
2012/0232599 A1 9/2012 Schoenly et al.
2012/0323284 A1 12/2012 Baker et al.
2013/0018426 A1 1/2013 Tsai et al.
2013/0046347 A1 2/2013 Cheng et al.
2013/0060291 A1 3/2013 Petersheim
2013/0123841 A1 5/2013 Lyon
2013/0138156 A1 5/2013 Derouet
2013/0150902 A1 6/2013 Leite
2013/0165981 A1 6/2013 Clasbrummet et al.
2013/0211463 A1 8/2013 Mizuno et al.
2013/0289630 A1 10/2013 Fritzinger
2014/0005728 A1 1/2014 Koay et al.
2014/0018862 A1 1/2014 Koay et al.
2014/0031879 A1 1/2014 Sixto, Jr. et al.
2014/0066998 A1 3/2014 Martin
2014/0094856 A1 4/2014 Sinha
2014/0121710 A1 5/2014 Weaver et al.
2014/0180345 A1 6/2014 Chan et al.
2014/0277178 A1 9/2014 O'Kane et al.
2014/0277181 A1 9/2014 Garlock
2014/0316473 A1 10/2014 Pfeffer et al.
2014/0330320 A1 11/2014 Wolter
2014/0378975 A1 12/2014 Castaneda et al.
2015/0051650 A1 2/2015 Verstreken et al.
2015/0051651 A1 2/2015 Terrill et al.
2015/0073486 A1 3/2015 Marotta et al.
2015/0105829 A1 4/2015 Laird
2015/0112355 A1 4/2015 Dahners et al.
2015/0134011 A1 5/2015 Medoff
2015/0142065 A1 5/2015 Schonhardt et al.
2015/0190185 A1 7/2015 Koay et al.
2015/0209091 A1 7/2015 Sixto, Jr. et al.
2015/0216571 A1 8/2015 Impellizzeri
2015/0223852 A1 8/2015 Lietz et al.
2015/0272638 A1 10/2015 Langford
2015/0282851 A1 10/2015 Michel
2015/0313653 A1 11/2015 Ponce et al.
2015/0313654 A1 11/2015 Horan et al.
2015/0327898 A1 11/2015 Martin
2015/0351816 A1 12/2015 Lewis et al.
2015/0374421 A1 12/2015 Rocci et al.
2016/0022336 A1 1/2016 Bateman
2016/0030035 A1 2/2016 Zajac et al.
2016/0045237 A1 2/2016 Cerynik et al.
2016/0045238 A1 2/2016 Bohay et al.
2016/0074081 A1 3/2016 Weaver et al.

(56) References Cited

U.S. PATENT DOCUMENTS

| | | | |
|---|---|---|---|
| 2016/0166297 | A1 | 6/2016 | Mighell et al. |
| 2016/0166298 | A1 | 6/2016 | Mighell et al. |
| 2016/0183990 | A1 | 6/2016 | Koizumi et al. |
| 2016/0262814 | A1 | 9/2016 | Wainscott |
| 2016/0278828 | A1 | 9/2016 | Ragghianti |
| 2016/0310183 | A1 | 10/2016 | Shah et al. |
| 2016/0310185 | A1 | 10/2016 | Sixto et al. |
| 2016/0324552 | A1 | 11/2016 | Baker et al. |
| 2016/0354122 | A1 | 12/2016 | Montello et al. |
| 2017/0035478 | A1 | 2/2017 | Andermahr et al. |
| 2017/0042592 | A1 | 2/2017 | Kim |
| 2017/0042596 | A9 | 2/2017 | Mighell et al. |
| 2017/0049493 | A1 | 2/2017 | Gauneau et al. |
| 2017/0065312 | A1 | 3/2017 | Lauf et al. |
| 2017/0105775 | A1 | 4/2017 | Ricker et al. |
| 2017/0215931 | A1 | 8/2017 | Cremer et al. |

FOREIGN PATENT DOCUMENTS

| | | | |
|---|---|---|---|
| CN | 202821574 | U | 3/2013 |
| CN | 202821575 | U | 3/2013 |
| CN | 203506858 | U | 4/2014 |
| CN | 203815563 | U | 9/2014 |
| CN | 105982727 | A | 10/2016 |
| EP | 3213703 | A2 | 9/2017 |
| FR | 2279371 | | 2/1976 |
| FR | 2595045 | | 2/1986 |
| FR | 2846870 | A1 | 5/2004 |
| FR | 2928259 | A1 | 9/2009 |
| JP | 62-253046 | A | 11/1987 |
| JP | 2003210478 | A | 7/2003 |
| JP | 2004344365 | A | 12/2004 |
| TW | 201316942 | A | 5/2013 |
| WO | 8701625 | | 10/1987 |
| WO | 2014055202 | A1 | 4/2014 |
| WO | 2015137976 | A1 | 9/2015 |
| WO | 2016079504 | A1 | 5/2016 |

* cited by examiner

FIXATORS FOR BONE STABILIZATION AND ASSOCIATED SYSTEMS AND METHODS

CROSS REFERENCE TO RELATED APPLICATIONS

This application is a continuation application of U.S. patent Ser. No. 17/676,304, is a continuation application of U.S. patent application Ser. No. 16/411,388 filed on May 14, 2019, which is a continuation application of U.S. patent application Ser. No. 15/708,193, filed on Sep. 19, 2017 (published as U.S. Pat. Pub. No. 2018-0000519), which is a continuation application of U.S. patent application Ser. No. 15/058,372, filed Mar. 2, 2016 (now U.S. Pat. No. 9,795, 411). The disclosures referenced above are being incorporated herein by reference in their entirety.

TECHNICAL FIELD

The present technology is generally related to fixators for stabilization of fractured bones.

BACKGROUND

For background purposes, a ring fixator is a stabilization device that is used on patients to treat complex and/or open bone fractures. The ring fixator is comprised of pins and wires secured to external scaffolding to provide support to a limb. This allows a bone or joint to be stabilized (e.g., via fusion) during trauma or limb reconstruction.

A ring fixator can be formed by a plurality of rings that are fixed to bone via tensioned pins or wires. The ring fixator can be used, for example, in fractured areas of high severity (e.g., with gunshot wounds), whereby traditional fixators are incapable of stabilizing the tissue. The ring fixators can remain in place until bone or joint stabilization is complete, upon which they can be removed.

SUMMARY

In one aspect of the present invention, a ring fixator assembly is disclosed. The ring fixator assembly includes a ring configured to surround a bone, a retention device disposed at a first position on the ring, a tensioner clamp disposed at a second position on the ring, and a wire extending between the retention device and the tensioner clamp. The tensioner clamp includes a clamping member configured to secure the wire in position with respect to the tensioner clamp and a tensioning member configured to apply tension to the wire.

In another aspect of the present invention, a tensioner clamp for a ring fixator assembly is disclosed. The tensioner clamp includes a central passage configured to receive a wire therein, a clamping member configured to secure the wire in position within the central passage, and a tensioning member configured to apply tension to the wire after the clamping member has secured the wire in position.

DETAILED DESCRIPTION

Figure 1:
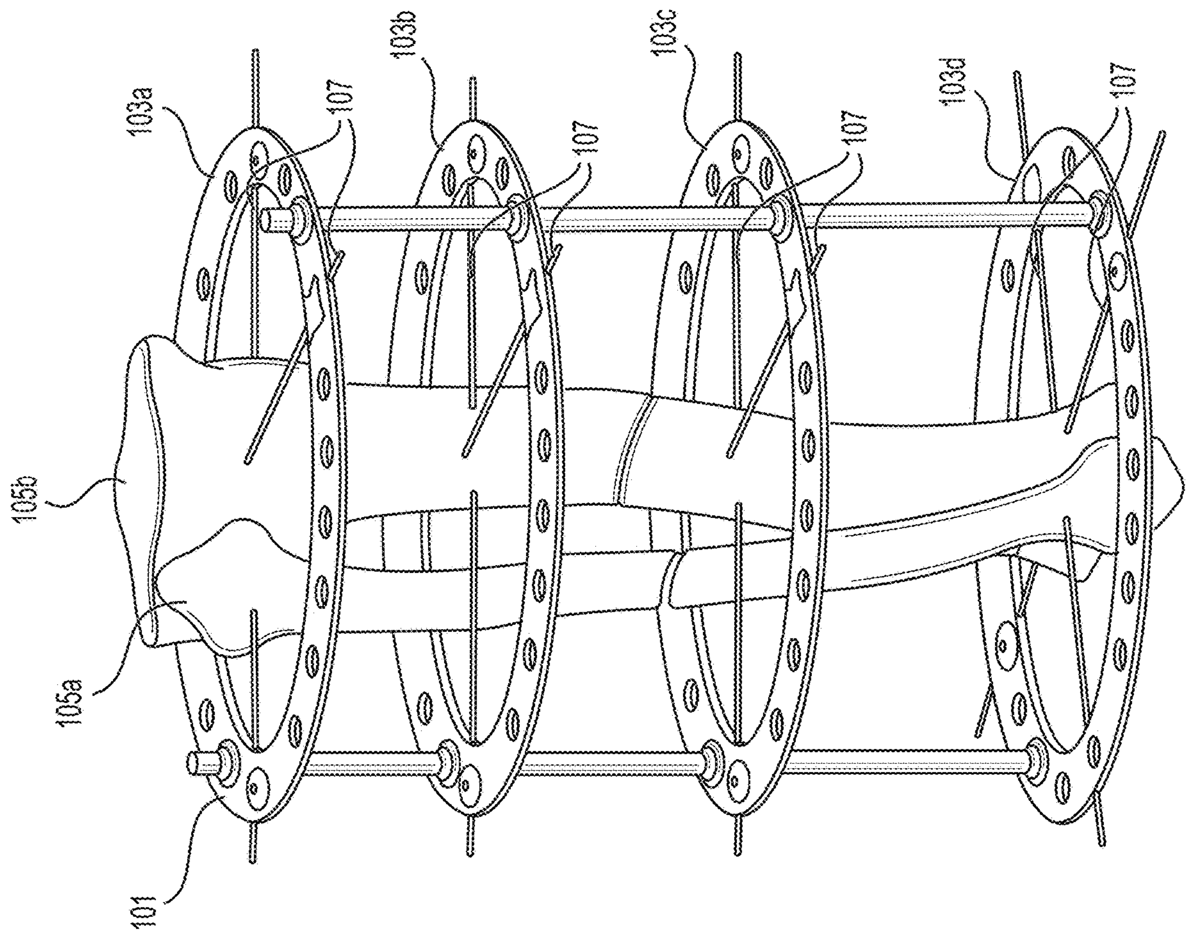
FIG. 1 is a schematic illustration of a ring fixator assembly.

The present disclosure relates to improved ring fixators. An example of a ring fixator is shown in FIG. 1. The ring fixator 101 includes multiple rings 103*a-d* that surround a patient's fractured bones 105*a*, 105*b*. A plurality of wires 107 extend across the individual rings 103*a-d*, passing through the bones 105*a*, 105*b*, thereby providing stability to the fractured bones 105*a*, 105*b* while the fractured bones are healed (e.g., via fusion). The ring fixator 101 can be positioned on the patient for as long as necessary until stabilization (e.g., via fusion) is achieved.

As shown in FIG. 1, each of the rings 103*a-d* of the ring fixator 101 can include one or more wires 107 that are attached to a ring member. To attach the one or more wires 107 to their respective ring member 103*a-d*, each of the wires would first be clamped to the ring member (e.g., via a clamping instrument). Following attachment, the one or more wires 107 would then be placed in tension (e.g., via a tensioner). These steps would involve two instruments-namely the clamping instrument for attachment and the tensioner for tensioning. The use of two instruments to perform multiple steps can be time consuming in an operation room, as a surgeon would have to first seek out a clamping instrument and then a tensioner for each location on the ring wherein a wire is attached.

Figure 2:
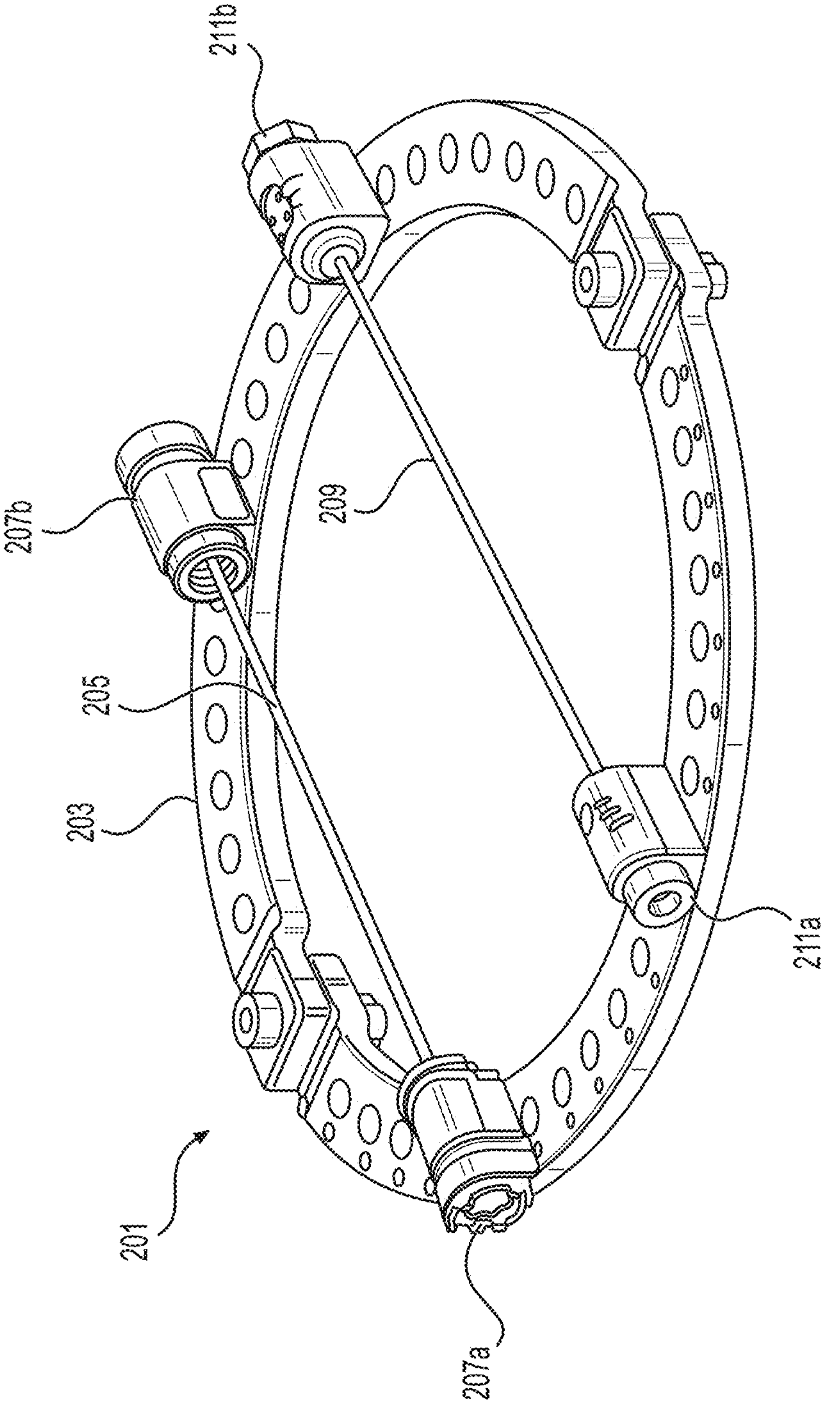
FIG. 2 illustrates a ring fixator including first and second tensioner clamps in accordance with an embodiment of the present technology.

The present disclosure is related to embodiments of an improved ring fixator utilizing a combined clamp and tensioner ("tensioner clamp"), which reduces a need to have both a clamping instrument and a separate tensioning instrument. Advantageously, in some embodiments, a single instrument can be used with the tensioner clamp, thereby saving valuable time in an operating room. FIGS. 2-6 show different embodiments of an improved tensioner clamp in accordance with some embodiments. In particular, as shown in FIG. 2, a ring fixator assembly 201 can utilize one or more types of tensioner clamps. One type of tensioner clamp 207*a*, 207*b* is shown attached to wire 205, while a second type of tensioner clamp 211*a*, 211*b* is shown attached to wire 209.

FIG. 2 illustrates a ring 203 of a ring fixator assembly 201 ("ring fixator 201") having four tensioner clamps affixed around the perimeter of the ring 203. A first wire 205 extends between two of a first type of tensioner clamp 207*a*, 207*b*, while a second wire 209 extends between two of a second type of tensioner clamp 211*a*, 211*b*. Each of the tensioner clamps 207 and 211 are configured to both clamp the wires 205 and 209 in place and to apply tension to the wires 205 and 209 after they have been clamped. In some embodiments, a single instrument can be used for both clamping and tensioning, thereby eliminating the need for multiple instruments.

The first and second tensioner clamps 207 and 211 are described in more detail below. Although the embodiment illustrated in FIG. 2 includes first and second tensioner clamps 207 and 211, in other embodiments the ring fixator may include only one type of tensioner clamp. In addition, in some embodiments the wire can be secured at one end by a simple retention device (e.g., a clamp device that cannot apply additional tension), while the wire is secured at the other end by a tensioner clamp. In additional embodiments, the term retention clamp can apply not only to a clamp that cannot apply additional tension, but also to a tensioner clamp. A first tensioner clamp 207 is shown in FIGS. 3A-3D, while a second tensioner clamp 211 is shown in FIGS. 4A-4C. FIG. 3A is a perspective view of a first tensioner clamp 207 engaging the wire 205 in accordance with some embodiments. As illustrated, the first tensioner clamp 207 includes a clamping screw 301 coaxial with a tensioning screw 303. A first driver (not shown) can be used to rotate the clamping screw 301, which causes a clamping member to secure the inner wire 205. A second driver (not shown) can then be used to rotate the tensioning screw 303, which causes tension to be applied to the inner wire 205. In other embodiments, a single driver can be used to control both the clamping screw 301 and the tensioning screw 303, thereby reducing the need for two separate drivers. In other embodiments, a single instrument can house a first driver for operating the clamping screw 301 and a second driver for operating the tensioning screw 303, thereby advantageously allowing a single instrument to perform both clamping and tensioning.

Figure 3B:
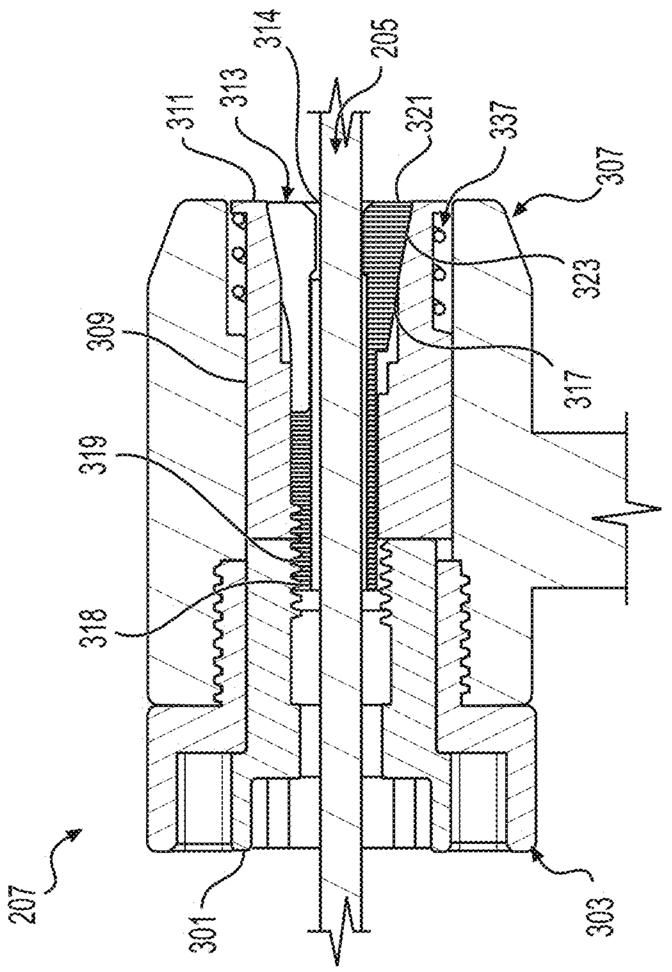
FIGS. 3A-3D illustrate various views of the first tensioner clamp configured in accordance with an embodiment of the present technology.
Figure 3A:
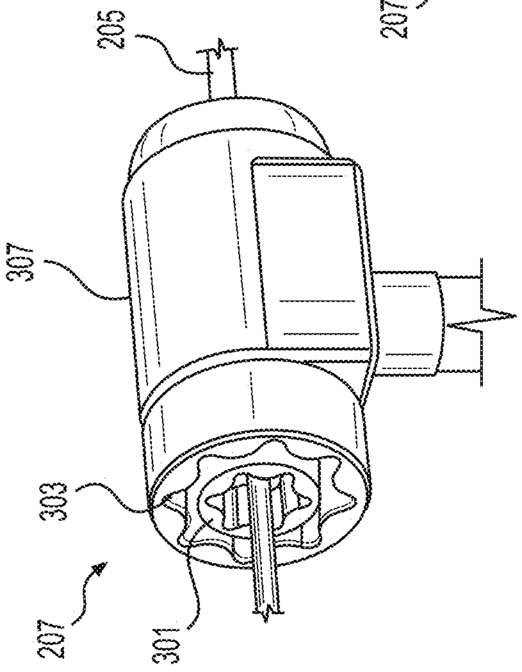
Figure 3C:
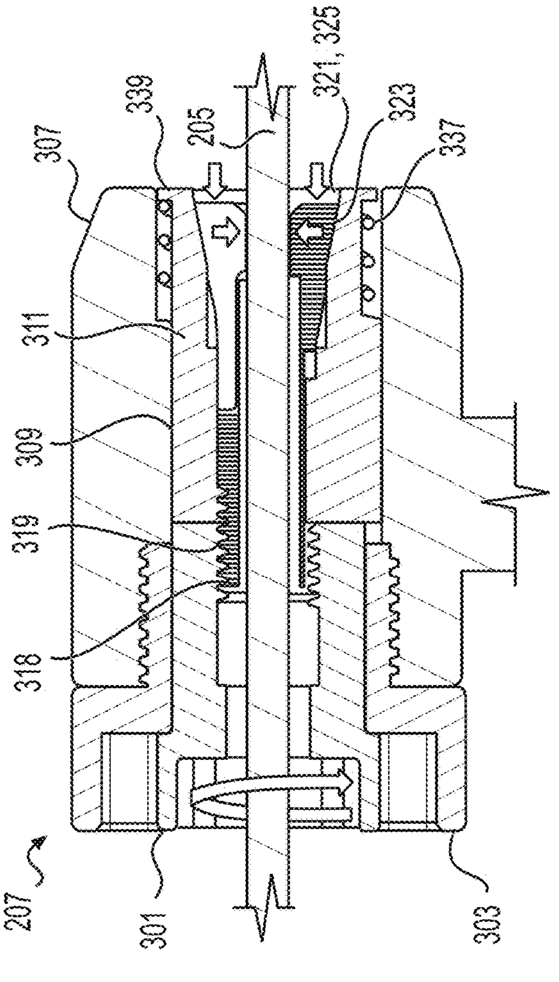
Figure 3D:
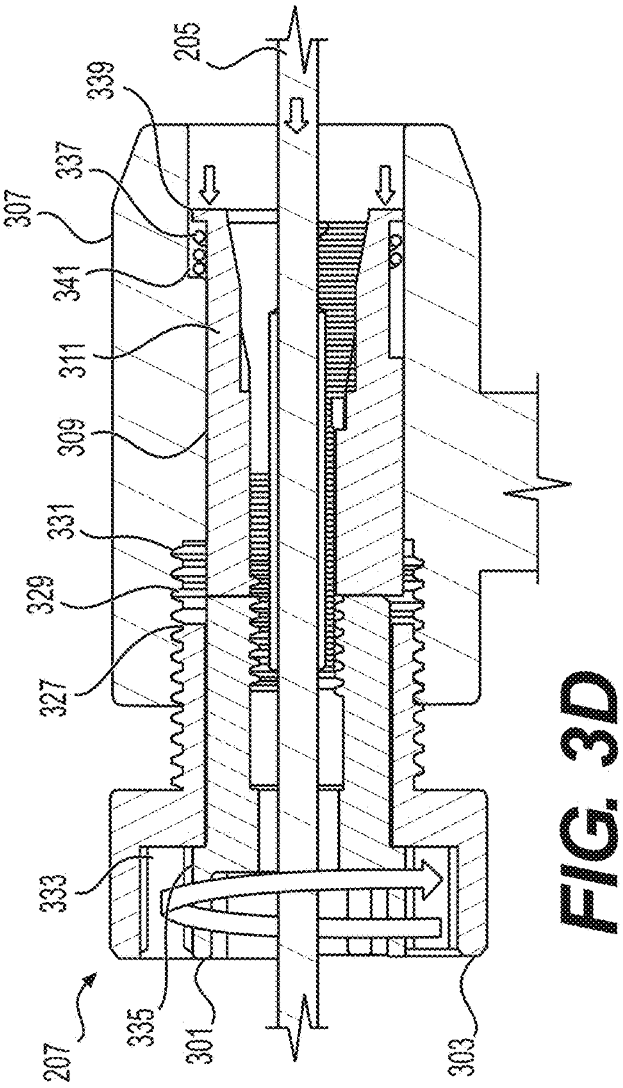
Figure 4A:
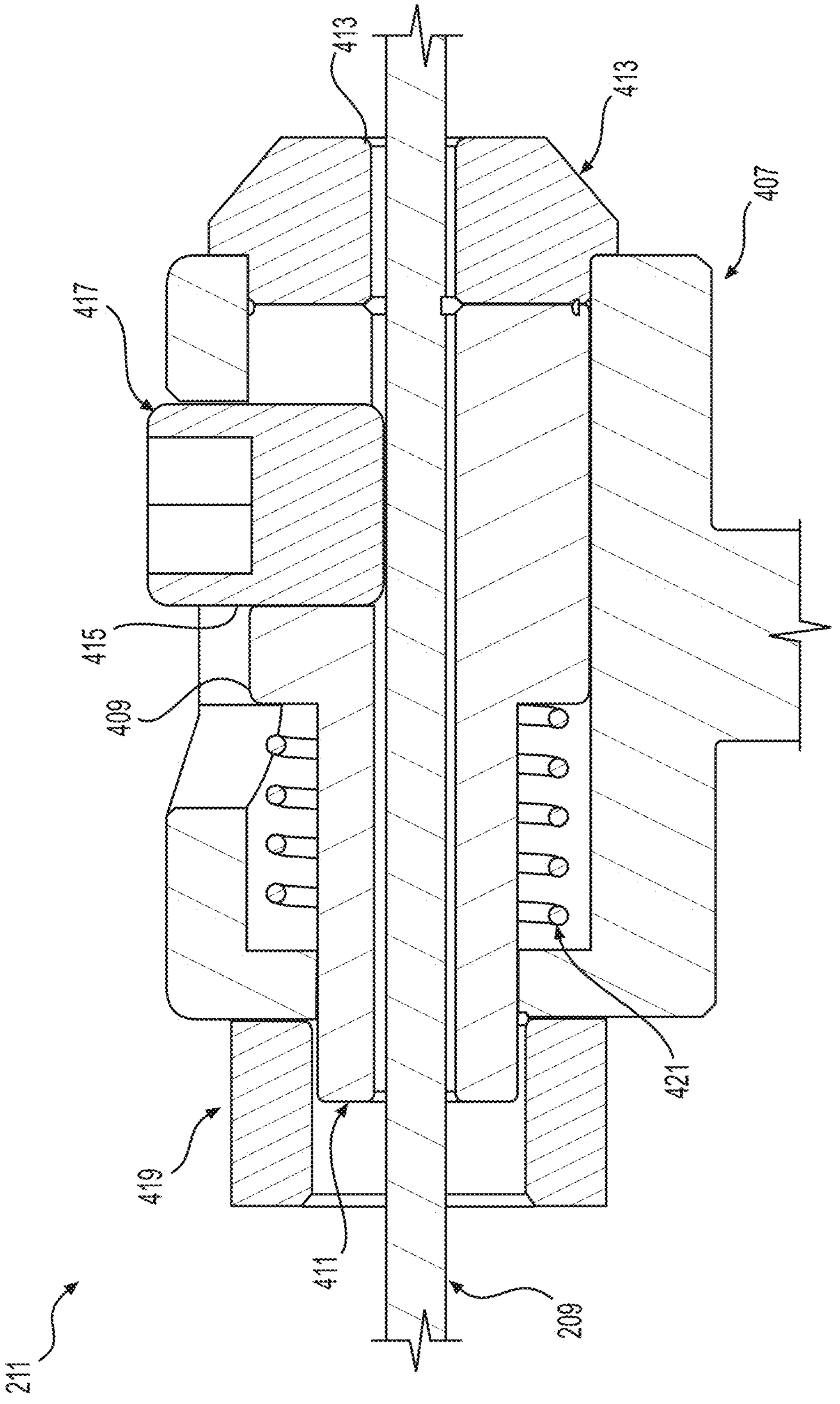
FIGS. 4A-4C illustrate various views of the second tensioner clamp configured in accordance with an embodiment of the present technology.
Figure 4C:
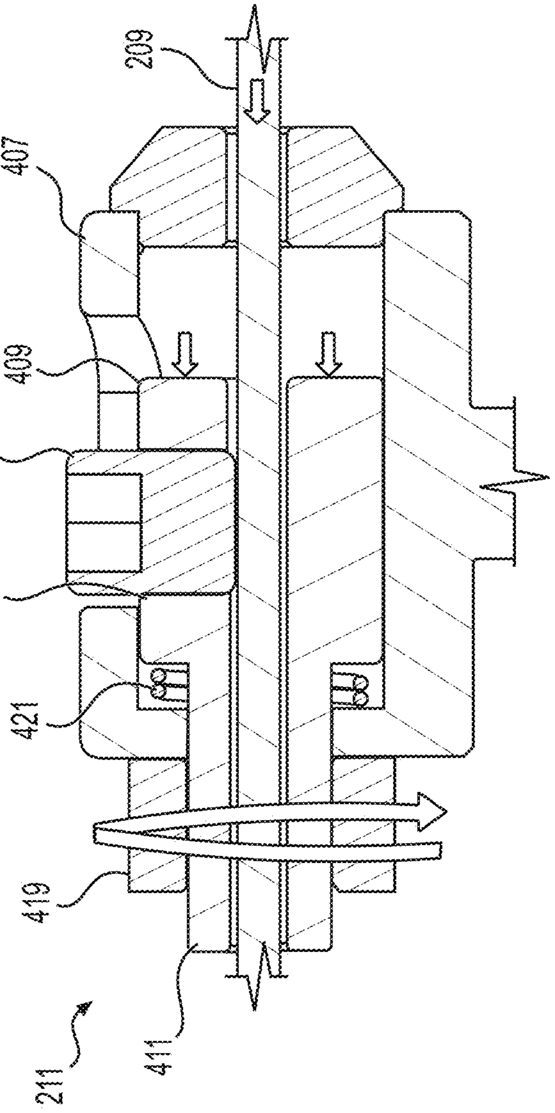
Figure 4B:
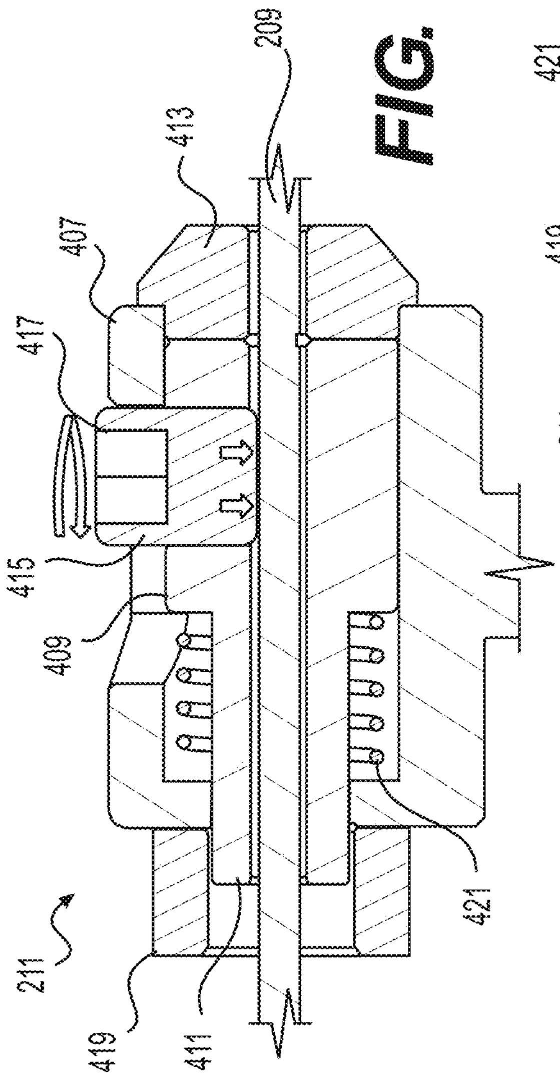

FIGS. 3B-3D illustrate side cross-sectional views of the first tensioner clamp 207 engaged with the wire 205 during different points of operation of the first tensioner clamp 207. In particular, FIG. 3B illustrates the first tensioner clamp 207 prior to clamping the wire 205, FIG. 3C illustrates the first tensioner clamp 207 after clamping the wire 205, and FIG. 3D illustrates the first tensioner clamp 207 after both clamping and tensioning the wire 205.

Referring to FIG. 3B, the first tensioner clamp 207 includes an outer housing 307. The housing 307 can be configured to be fixedly attached to a ring of a ring fixator. Within the housing 307 is a clamping assembly 309 which clamps the wire 205 in place in response to rotation of the clamping screw 301. The clamping assembly 309 includes a collet housing 311 received within the outer housing 307 and a collet 313 received within the collet housing 311. The collet 313 has a central opening 314 to receive the wire 205 therein, and includes a proximal end portion 315 and a distal end portion 317 opposite to the proximal end portion 315. The proximal end portion 315 includes threads 318 that are configured to engage with corresponding threads 319 of the clamping screw 301. The distal end portion 317 includes a compressible member 321 that engages with an angled surface 323 of the collet housing 311.

As illustrated in FIG. 3C, during operation, the clamping screw 301 is rotated, causing the collet 313 to be retracted relative to the collet housing 311. During this retraction, the compressible member 321 of the collet 313 engages with the angled surface 323 of the collet housing 311, thereby causing the compressible member 321 to press inwardly onto the wire 205, effectively clamping the wire 205 in place. In the illustrated embodiment, the compressible member 321 takes the form of a plurality of flared portions 325 separated by gaps such that these flared portions can be drawn inwardly radially together by engagement with the angled surface 323 of the collet housing 311 until the flared portions 325 come into contact with the wire 205.

Once the wire 205 has been clamped into position by rotation of the clamping screw 301, the wire 205 can be tensioned. Referring to FIG. 3D, the tensioning screw 303 includes distal threads 327 that are threadably engaged with corresponding threads 329 on an interior surface 331 of the housing 307. Rotation of the tensioning screw 303 causes the tensioning screw 303 to retract relative to the housing 307. The tensioning screw 303 is engaged with the clamping assembly 309 such that when the tensioning screw 303 is retracted relative to the housing 307, the clamping assembly 309 and the clamping screw 301 are also retracted. For example, a proximal surface 333 of the tensioning screw 303 can engage with a flange 335 of the clamping screw 301. The tensioning screw 303 can also be engaged with the clamping assembly 309 via internal threads (not shown). Accordingly, when the tensioning screw 303 is retracted from the housing 307, the proximal surface 333 of the tensioning screw contacts the flange 335 of the clamping screw 301, thereby causing the clamping screw 301 (and, correspondingly, the clamping assembly 309) to be retracted as well. As the clamping assembly 309 is clamped on the wire 205, retraction of the clamping assembly 309 increases tension in the wire 205.

In some embodiments, a spring 337 is disposed around the collet housing 311 between a distal flange 339 of the collet housing 311 and an engagement surface 341 of the interior surface 331. When compressed, this spring 337 urges the collet housing 311 (and, correspondingly, the clamping assembly 309) in a distal direction. This countervailing force provided by the spring 337 can provide for increased control in the amount of tension applied to the wire 205 during rotation of the tensioning screw 303.

FIGS. 4A-4C illustrate side cross-sectional views of a second tensioner clamp 211 in accordance with some embodiments. The second tensioner clamp 211 is engaged with the wire 209 during different points of operation of the second tensioner clamp 211. In particular, FIG. 4A illustrates the second tensioner clamp 211 prior to clamping the wire 209, FIG. 4B illustrates the second tensioner clamp 211 after clamping the wire 209, and FIG. 4C illustrates the second tensioner clamp 211 after clamping and tensioning the wire 209.

The second tensioner clamp 211 can utilize many features similar to the first tensioner clamp 207 described above with respect to FIGS. 3A-3D, for example by providing combined clamping and tensioning capabilities. However, the particular configuration of the tensioner clamp 211 utilizes alternative mechanisms to clamp and to tension the wire 209 can differ.

Referring to FIG. 4A, the second tensioner clamp 211 includes an outer housing 407 surrounding a clamping assembly 409. The outer housing 407 can be configured to be fixedly coupled to a ring of a ring fixator. The clamping assembly 409 includes a clamp body 411 with a central opening 413 that receives the wire 209 therethrough. A radial aperture 415 in the clamp body 411 is oriented transversely with respect to the central opening 413. For example, in some embodiments the aperture 415 can be perpendicular to the central opening 413. A clamping screw 417 (e.g., a set screw) can be threadably engaged with the aperture 415 and configured to be rotated to apply downward pressure onto the wire 209, as illustrated in FIG. 4B. Rotation of the clamping screw 417 into this position can clamp the wire 209 into position with respect to the clamping assembly 409.

Referring to FIG. 4C, the second tensioner clamp 211 includes a tensioning nut 419 that is threadably engaged with the clamp body 411 such that rotation of the tensioning nut 419 causes the clamp body 411 to be retracted with respect to the housing 407, thereby applying tension to the wire 209. In some embodiments, the second tensioner clamp 211 further includes a spring 421 surrounding a portion of the clamp body 411 and configured to urge the clamp body 411 away from the tensioning nut 419 when the clamp body 411 is retracted with respect to the housing 407. This countervailing force provided by the spring 421 can provide for increased control in the amount of tension applied to the wire 205.

In operation, a first driver (not shown) can be used to rotate the clamping screw 417, which causes is the clamping screw 417 to be downwardly threaded through the aperture 415 until it presses upon the wire 209 with sufficient pressure to clamp the wire 209 in place. A second driver (not shown) can then be used to rotate the tensioning nut 419, which causes tension to be applied to the wire 209. The tensioning nut 419 can be rotated to gradually increase and decrease the applied tension to the wire 209. The tensioning nut 419 can be rotated until the desired tension is applied to the wire 209. Rotation of the tensioning nut 419 in the opposite direction causes tension to be reduced on the wire 209. In other embodiments, a single driver can be used to control both the clamping screw 417 and the tensioning nut 419, thereby reducing the need for two separate drivers. In other embodiments, a single instrument can house a first driver for operating the clamping screw 417 and a second driver for operating the tensioning nut 419, thereby advantageously allowing a single instrument to perform both clamping and tensioning.

Often times, when attaching a ring fixator to a patient, one individual must hold a ring, while another extends the wires through the patient. Without an individual holding the ring, the ring fixator can slip and become disengaged during application. It has been found that providing a ring with a soft tissue spacer formed therein can help to retain the ring on the patient. The soft tissue spacer is advantageously designed to be removable such that once the ring of the ring fixator is put in place, it can be removed. By providing such a soft tissue spacer, this reduces the reliance on an individual having to hold the ring during installation of the ring fixator.

Figure 5:
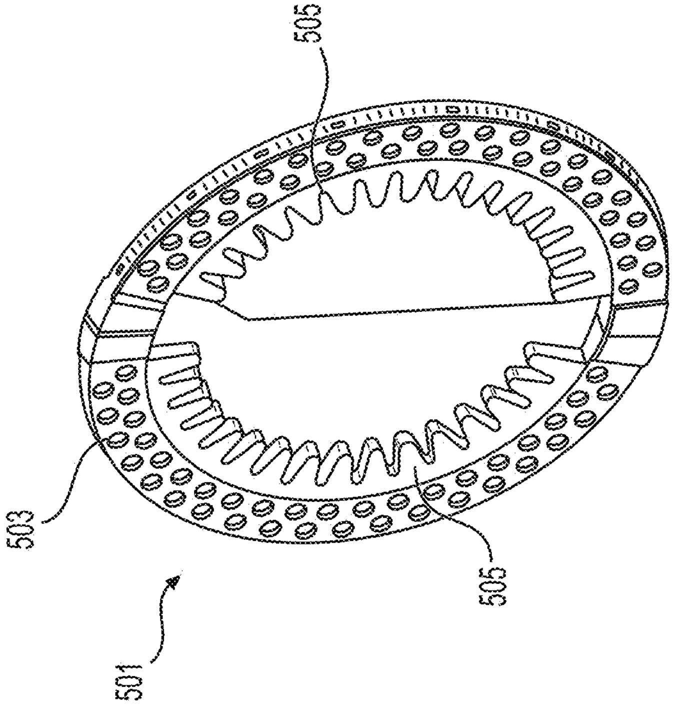
FIG. 5 illustrates a ring fixator with a soft tissue spacer in accordance with an embodiment of the present technology.

FIG. 5 illustrates a perspective view of a ring fixator 501 having a ring 503 and a spacer 505 coupled to the ring. The spacer 505 coupled to the ring can alleviate the need to rely on someone to hold the ring during installation. In some embodiments, the spacer 505 can be made of foam or other soft material, and can extend radially inwardly from the ring 503 so as to engage the anatomy of the patient. Providing a ring 503 with a soft tissue spacer 505 formed therein advantageously reduces the need to have an additional person hold the ring in place while applying the ring fixator. In addition, as the spacer 505 is formed of a soft material (e.g., foam), this provides added comfort to a patient during installation. The soft tissue spacer 505 can be removable such that once the ring fixator 501 is put in place, the spacer 505 can be removed. The soft tissue spacer 505 can be attached to the ring 503 via an adhesive or via nubs/protrusions that are insertable into openings in the ring. In some embodiments, the spacer 505 can be attached to the ring via an adhesive or via nubs/protrusions that are insertable into openings in the ring, thereby making it easy to attach and remove the spacer 505 from the ring.

As shown in FIG. 5, one or more spacers 505 can be attached to different segments of the inner wall of a ring. In the present embodiment, a first spacer is attached to one side of the ring, while a second spacer is attached to a second side of the ring. By providing a first spacer that is independent from a second spacer, this facilitates ease of attachment of the spacers within the ring. In addition, as shown in FIG. 5, each of the spacers can include recesses. These recesses can be in contact with the patient, and can advantageously help to accommodate varying patient anatomy.

Often times, a ring of a ring fixator (e.g., composed of two half circles) can be attached to a patient via bolts or screws. As the ring fixator is composed of multiple rings, it can be time consuming to perform the operation. It has been found that it is possible to reduce the time of the operation by providing various quick-connect mechanisms that allow a ring of a ring fixator to be attached to a patient quickly.

Figure 6:
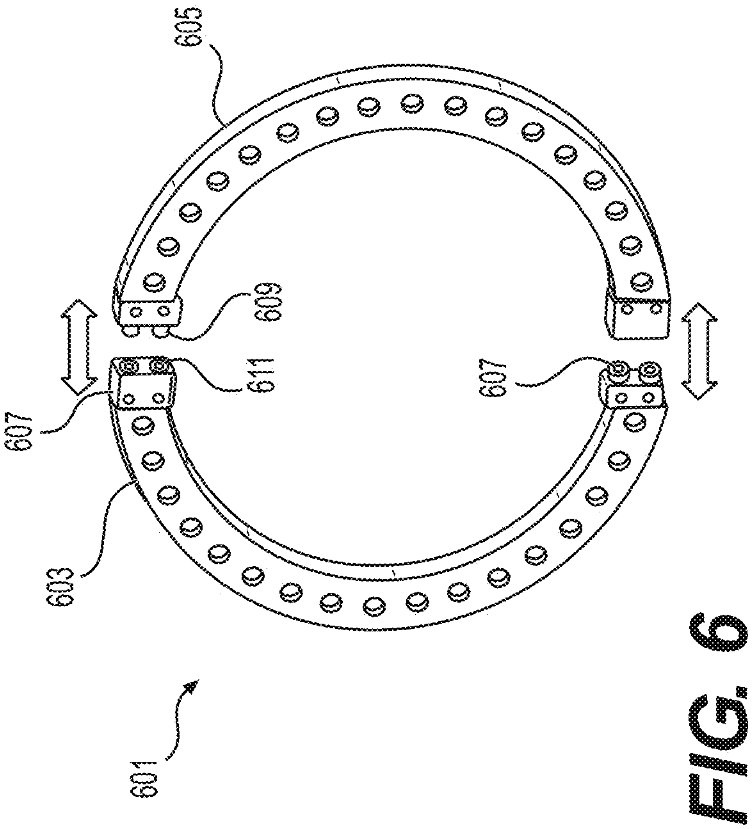
FIG. 6 illustrates a ring fixator with quick-connect segments in accordance with an embodiment of the present technology.

FIG. 6 illustrates a ring 601 having first and second members 603 and 605 joined by quick-connect components 607. The quick-connect components 607 shown in FIG. 6 advantageously allow the first and second members 603 and 605 to be secured together quickly. In the illustrated embodiment, the quick-connect components 607 include pins 609 and corresponding recesses 611 to receive the pins 609 therein. The quick-connect components 607 can take various other forms, such as mateable notches and protrusions, grooves and nubs, etc. In some embodiments, the quick-connect components 607 can include magnetic holding features in addition to or in lieu of mechanical mating features. In some embodiments, the two members 603 and 605 can be connected using these quick connect components 607 in addition to traditional screws, thereby forming a way to rapidly secure the two members 603 and 605 together while initially applying the ring fixator to a patient, while still allowing for a more robust fixation to be applied at a later stage through the use of screws.

Although many of the embodiments are described above with respect to devices, systems, and methods for ring fixators, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein. In particular, the ring fixators can be combined and used with other types of fixators, including rod fixators. In addition, the ring fixators can be used with various components used to heal bone fractures, including but not limited to, plates, rods, and screws.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term “comprising” is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A ring fixator assembly comprising:
- a ring configured to surround a bone;
- a first retention device disposed at a first position on the ring;
- a first tensioner clamp disposed at a second position on the ring;
- a second tensioner clamp disposed at a third position on the ring;
- a second retention device disposed at a fourth position on the ring; and
- a first wire extending between the first retention device and the first tensioner clamp;
- a second wire extending between the second retention device and the second tensioner clamp;
- wherein the first tensioner clamp comprises a first housing including a first clamping member therein configured to secure the first wire in position with respect to the first tensioner clamp and a first tensioning member configured to apply tension to the first wire, wherein rotation of the tensioning member causes the tensioning member to retract away from the first housing, thereby causing tension on the first wire and
- wherein the second tensioner clamp comprises a second housing including a clamping member therein configured to secure the second wire in position with respect to the second tensioner clamp and a second tensioning member configured to apply tension to the second wire, wherein rotation of the tensioning member causes the tensioning member to retract away from the second housing, thereby causing tension on the second wire.

2. The ring fixator assembly of claim 1, wherein the first and second clamping members each comprise a clamping screw and wherein the first and second tensioning member each comprise a tensioning screw, and wherein clamping screw and the tensioning screw are configured to be controlled by a single driver.

3. The ring fixator assembly of claim 1, wherein the first and second housings each surround a clamping assembly, the clamping assembly comprising:
- a collet housing; and
- a collet received at least partially within the collet housing,
- wherein a respective wire passes through a central opening in the collet,
- wherein a respective clamping member comprises a clamping screw threadably engaged with the collet such that rotation of the clamping screw causes the collet to be drawn into the collet housing, thereby clamping the respective wire, and
- wherein a respective tensioning member comprises a tensioning screw threadably engaged with the first or second housing and coupled to the clamping assembly such that rotation of the tensioning screw causes the clamping assembly to be drawn away from a respective retention device, thereby applying tension to the respective wire.

4. The ring fixator assembly of claim 3, wherein the collet comprises a compressible end portion that compresses when drawn into the collet housing, thereby clamping the respective wire.

5. The ring fixator assembly of claim 3, wherein the tensioning screw is coaxial with the clamping screw.

6. The ring fixator assembly of claim 1, wherein the ring comprises:
- a first ring portion;
- a second ring portion; and
- a quick-connect assembly that releasably couples the first ring portion to the second ring portion.

7. The ring fixator assembly of claim 1, wherein the quick-connect assembly comprises first magnetic features disposed on ends of the first ring portion and second magnetic features disposed on ends of the second ring portion, the first and second magnetic features configured to be magnetically joined together.

8. The ring fixator assembly of claim 1, further comprising a spacer coupled to the ring and extending radially inwardly from the ring, the spacer configured to engage a patient’s anatomy when the ring is positioned around a patient’s limb.

9. A ring fixator assembly comprising:
- a ring configured to surround a bone;
- a first retention device disposed at a first position on the ring;
- a first tensioner clamp disposed at a second position on the ring;
- a second tensioner clamp disposed at a third position on the ring;
- a second retention device disposed at a fourth position on the ring; and
- a first wire extending between the first retention device and the first tensioner clamp;
- a second wire extending between the second retention device and the second tensioner clamp;
- wherein the first tensioner clamp comprises a first housing including a first clamping member therein configured to secure the first wire in position with respect to the first tensioner clamp and a first tensioning member configured to apply tension to the first wire, wherein rotation of the tensioning member causes the tensioning member to retract away from the first housing, thereby causing tension on the first wire and
- wherein the second tensioner clamp comprises a second housing including a clamping member therein configured to secure the second wire in position with respect to the second tensioner clamp and a second tensioning member configured to apply tension to the second wire, wherein rotation of the tensioning member causes the tensioning member to retract away from the second housing, thereby causing tension on the second wire,
- wherein each of the first and second tensioner clamps comprises:
  - a central passage configured to receive a respective wire therein;
  - a housing including the respective clamping member configured to secure the respective wire in position within the central passage; and the respective tensioning member configured to apply tension to the respective wire after the clamping member has secured the respective wire in position, wherein rotation of the tensioning member causes the tensioning member to retract away from the housing, thereby causing tension on the respective wire.

10. The ring fixator assembly of claim 9, wherein the clamping members each comprise a clamping screw and wherein the tensioning members each comprise a tensioning screw, and wherein the clamping screw and the tensioning screw are configured to be controlled by a single driver.

11. The ring fixator assembly of claim 10, wherein the tensioning screw is coaxial with the clamping screw.

12. The ring fixator assembly of claim 9, wherein the housing surrounds a clamping assembly, the clamping assembly comprising:

a collet housing; and a collet received at least partially within the collet housing, wherein the respective wire passes through a central opening in the collet, wherein the respective clamping member comprises a clamping screw threadably engaged with the collet such that rotation of the clamping screw causes the collet to be drawn into the collet housing, thereby clamping the respective wire.

13. The ring fixator assembly of claim 12, wherein the respective tensioning member comprises a tensioning screw threadably engaged with the housing and coupled to the clamping assembly such that rotation of the tensioning screw causes the clamping assembly to be drawn away from the respective retention device, thereby applying tension to the respective wire.

14. The ring fixator assembly of claim 12, wherein the collet comprises a compressible end portion that compresses when drawn into the collet housing, thereby clamping the respective wire.

15. The ring fixator assembly of claim 14, wherein the compressible end portion comprises flared portions separated by gaps.

* * * * *